US011589858B2

(12) United States Patent
Berry

(10) Patent No.: US 11,589,858 B2
(45) Date of Patent: Feb. 28, 2023

(54) SURGICAL RETRACTOR

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 16 days.

(21) Appl. No.: 17/185,183

(22) Filed: Feb. 25, 2021

(65) Prior Publication Data

US 2022/0265260 A1 Aug. 25, 2022

(51) Int. Cl.
 *A61B 17/02* (2006.01)
(52) U.S. Cl.
 CPC ...... *A61B 17/0293* (2013.01); *A61B 17/0206* (2013.01)
(58) Field of Classification Search
 None
 See application file for complete search history.

(56) References Cited

U.S. PATENT DOCUMENTS

| 1,428,653 A | * | 9/1922 | Nick | A61M 29/02 |
| | | | | 606/41 |
| 7,473,222 B2 | | 1/2009 | Dewey | |
| 2014/0114138 A1 | * | 4/2014 | Fedorov | A61B 17/0206 |
| | | | | 600/233 |
| 2014/0114139 A1 | * | 4/2014 | Ziolo | A61B 17/025 |
| | | | | 600/233 |

OTHER PUBLICATIONS

Complaint for Patent Infringement Case No. 18CV0347 GPC BLM filed by NuVasive, dated Feb. 13, 2018, in the United States District Court for the Southern District of California, San Diego Division.
EndoRing Surgical Retraction System User's Guide from Medtronic dated 1999.

* cited by examiner

*Primary Examiner* — Tessa M Matthews
(74) *Attorney, Agent, or Firm* — Ellenoff Grossman & Schole LLP; James M. Smedley; Alex Korona

(57) ABSTRACT

A method is disclosed. The method includes providing a plurality of blades, movably connecting the plurality of blades to an outer member via a plurality of arm members, disposing the plurality of blades in a human or animal body, and moving the plurality of blades from a first position outward to a second position when the plurality of blades are disposed in the human or animal body. The plurality of blades are disposed further from each other in the second position than the first position. Moving the plurality of blades outward from the first position to the second position includes moving the plurality of arm members. Moving the plurality of blades includes maintaining equidistance between the plurality of blades as the plurality of blades move from the first position to the second position.

18 Claims, 5 Drawing Sheets

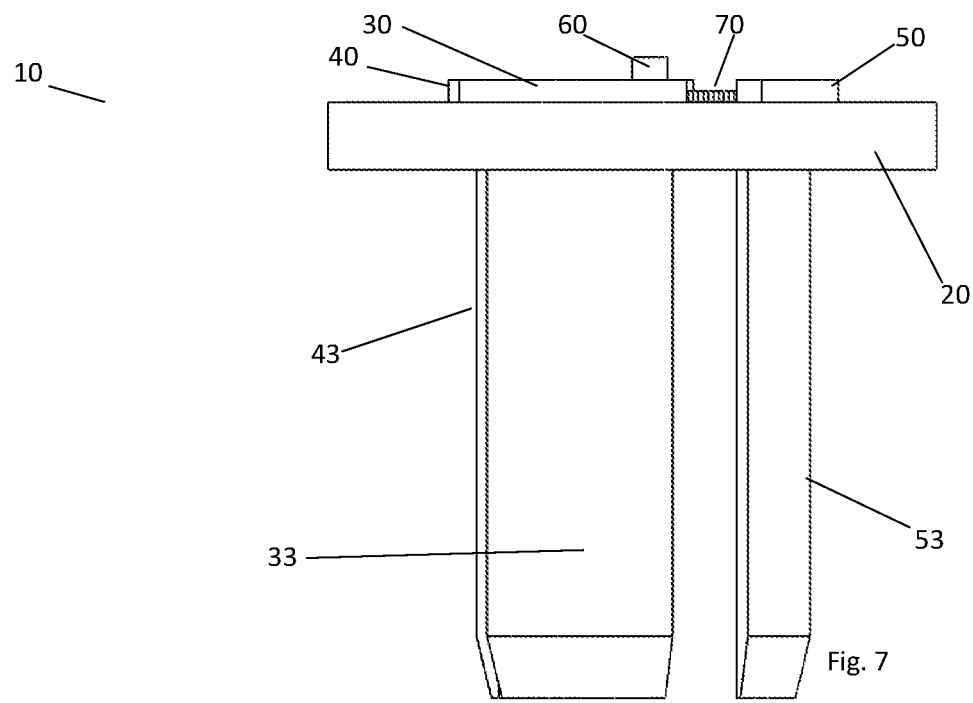
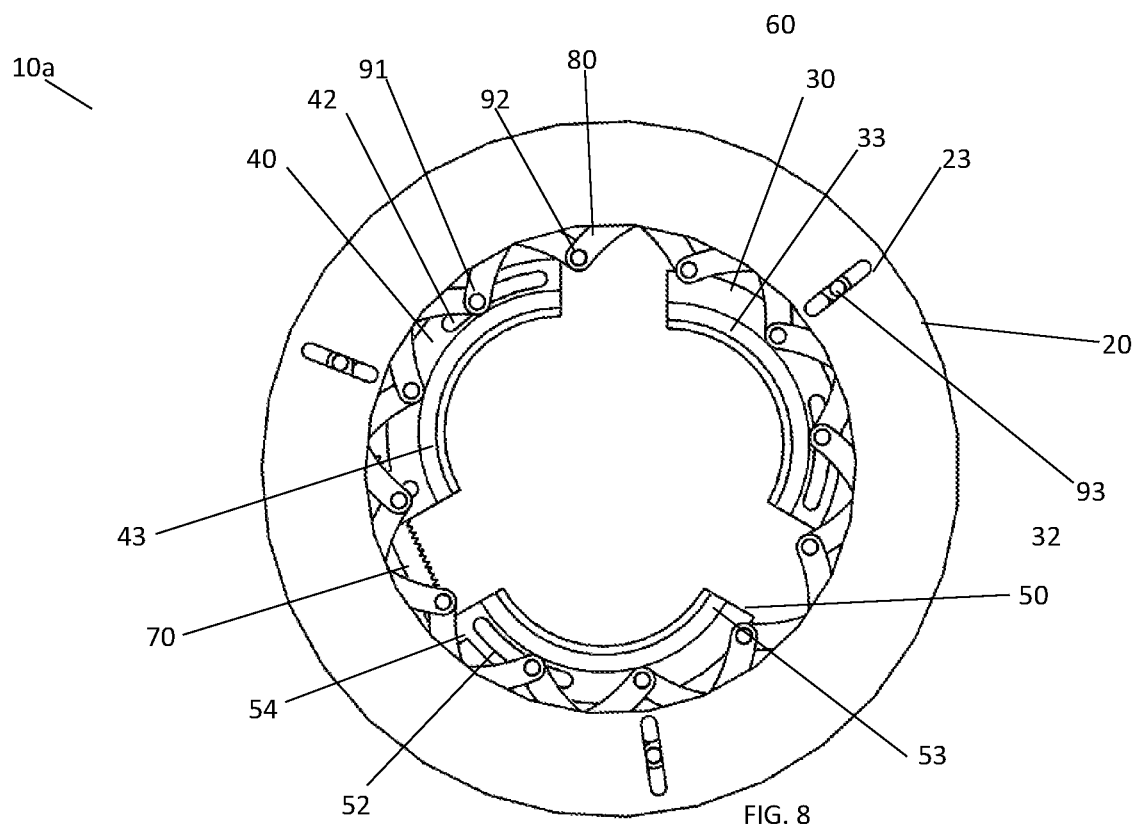

SURGICAL RETRACTOR

TECHNICAL FIELD

The present disclosure is directed to a retractor, and more particularly, to a surgical retractor.

BACKGROUND OF THE DISCLOSURE

Surgical retractors are used to hold an injured portion of a patient's body or incision open while a surgeon works on the patient. The surgical retractor thereby provides access for the surgeon during a surgical procedure at a given region of tissue.

Some soft tissue retractors are handheld, while others attach to a fixed ring. Conventional retractors are expandable, typically expanded by hand, one blade at a time. Some retractors are plier-type instruments, in which squeezing the handles of the instruments expands two of the blades of the instrument. However, these instruments typically have a third blade that is expanded separately from the other blades. Such conventional instruments may create uneven pressure on soft tissue, leading to bruising and post-surgical pain. Additionally, expanding the blades separately takes additional time during surgeries in which every precious second counts for providing positive patient outcomes.

Furthermore, such conventional retractors are typically large and bulky. Conventional retractors including a fixed ring are typically much larger than desired, to allow the blades of the instruments to slide. The plier-type retractors typically have larger metal handles. These large, bulky retractors can get in the way of the surgeon and may obstruct x-ray and other imaging that are performed during a procedure.

The exemplary disclosed system and method of the present disclosure is directed to overcoming one or more of the shortcomings set forth above and/or other deficiencies in existing technology.

SUMMARY OF THE DISCLOSURE

In one exemplary aspect, the present disclosure is directed to a method. The method includes providing a plurality of blades, movably connecting the plurality of blades to an outer member via a plurality of arm members, disposing the plurality of blades in a human or animal body, and moving the plurality of blades from a first position outward to a second position when the plurality of blades are disposed in the human or animal body. The plurality of blades are disposed further from each other in the second position than the first position. Moving the plurality of blades outward from the first position to the second position includes moving the plurality of arm members. Moving the plurality of blades includes maintaining equidistance between the plurality of blades as the plurality of blades move from the first position to the second position.

In another aspect, the present disclosure is directed to a retractor. The retractor includes an annular member including a hollow interior, a first blade, a gear blade, and a rack blade disposed in the hollow interior, a first plurality of arm members rotatably connecting the first blade to the annular member, a second plurality of arm members rotatably connecting the gear blade to the annular member, and a third plurality of arm members rotatably connecting the rack blade to the annular member. At least one of the first plurality of arm members is either attached to the first blade via a first slot pin that is configured to rotate and translate in a first pin slot of the first blade, or attached to the annular member via a first ring pin that is configured to rotate and translate in a first annular member pin slot of the annular member

BRIEF DESCRIPTION OF THE DRAWINGS

Accompanying this written specification is a collection of drawings of exemplary embodiments of the present disclosure. One of ordinary skill in the art would appreciate that these are merely exemplary embodiments, and additional and alternative embodiments may exist and still within the spirit of the disclosure as described herein.

FIG. 7 illustrates a lateral view of an exemplary disclosed retractor in an open position;

FIG. 8 illustrates a distal view of an exemplary disclosed retractor in an open position.

DETAILED DESCRIPTION AND INDUSTRIAL APPLICABILITY

Figure 1:
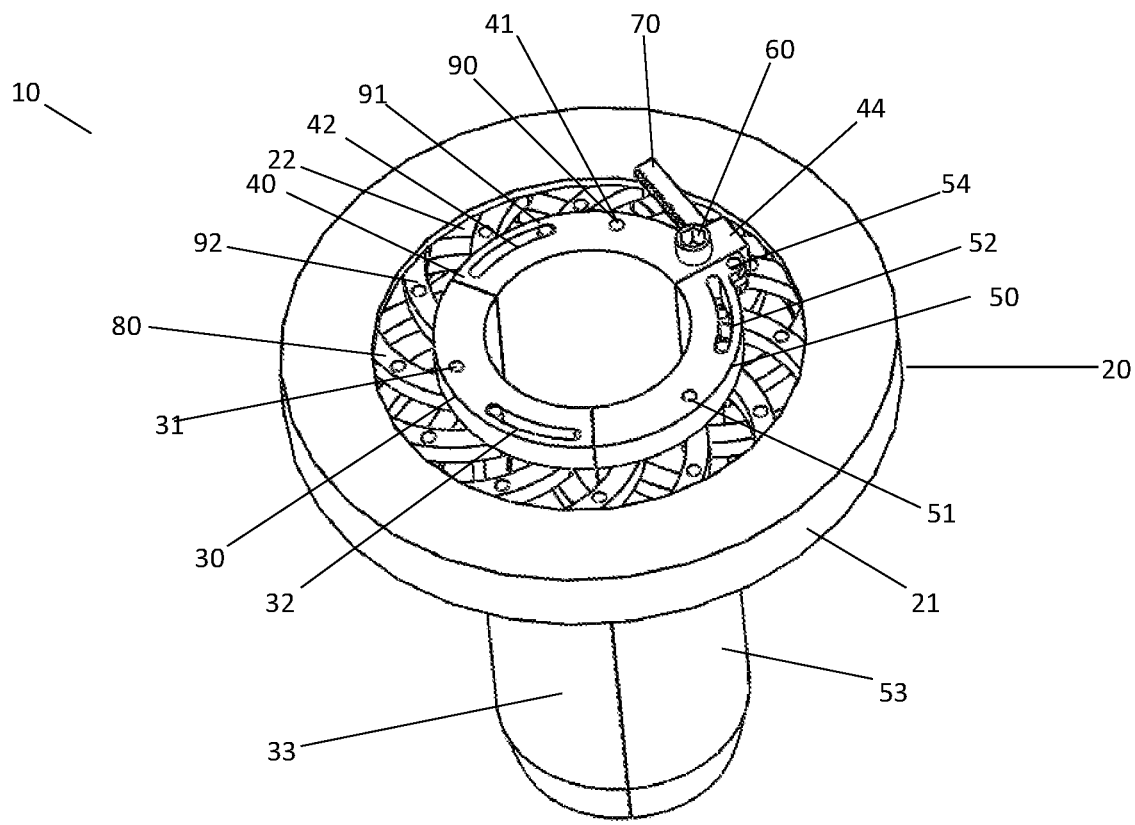
FIG. 1 illustrates a perspective view of a proximal face of an exemplary disclosed retractor.

The exemplary disclosed system, apparatus, and method may include a surgical retractor. For example, the exemplary disclosed system, apparatus, and method may be a lumbar retractor. In at least some exemplary embodiments, the exemplary disclosed system, apparatus, and method may include a soft tissue retractor that provides circumferential expansion.

In at least some exemplary embodiments, the exemplary disclosed system, apparatus, and method may be slid over a set of distractor tubes into an incision (e.g., a small incision) in the body. Once the exemplary disclosed retractor is disposed inside the surgical wound, the retractor may be expanded to allow suitable (e.g., better) access for a surgeon. In at least some exemplary embodiments, all blades may move in unison, which may create substantially equal pressure on the soft tissue. The exemplary disclosed retractor may be formed from any suitable material for providing a retractor such as, for example, stainless steel, other suitable metal material, and/or any other suitable structural materials for providing a retractor.

As illustrated in FIGS. 1-3, 5-7, and 9, a retractor 10 may include a number of components arrayed in a circular pattern. A member (e.g., member) such as an outer member (e.g., outer ring 20) may have an outer shell 21, with a hollow interior 22. Outer ring 20 may be an annular member having an elliptical or circular shape. A plurality of (e.g., a series of at least three) retractor blades 30, 40, and 50 may be disposed (e.g., located centrally) within the outer ring 20. Blade 30 may be a first blade (e.g., first blade 30), blade 40 may be a gear blade (e.g., gear blade 40), and blade 50 may be a rack blade (e.g., rack blade 50). The first blade 30 may include a pin hole 31, a curved pin slot 32 disposed on a proximal portion of first blade 30, and an elongated distal portion 33. The distal portion 33 may extend into a surgical wound of a patient (e.g., or animal) when the retractor 10 is disposed in the patient. The gear blade 40 may include a pin hole 41, a curved pin slot 42 disposed on a proximal portion of gear blade 40, and an elongated distal portion 43. The distal portion 43 may extend into a surgical wound of a patient (e.g., or animal) when the retractor 10 is disposed in the patient. The rack blade 50 may include a pin hole 51, a curved pin slot 52 disposed on a proximal portion of rack blade 50, and an elongated distal portion 53. The distal portion 53 may extend into a surgical wound of a patient when the retractor 10 is disposed in the patient.

As illustrated in FIGS. 1-3, 5-7, and 9, the gear blade 40 may include a rack guide 44 disposed at an outer circumference of the proximal side of the gear blade 40. Rack guide 44 may guide a rack 70. For example, the rack guide 44 may be configured to receive (e.g., interact with, mesh with, and/or receive in any other suitable manner) and/or guide rack 70. Also for example, the gear blade 40 may include a gear aperture (e.g., a gear hole 45) disposed on the proximal face of gear blade 40. The gear hole 45 may house a gear 60 (e.g., gear 60 component). The gear hole 45 of the gear blade 40 may intersect (e.g., be integral with) the rack guide 44, allowing the gear 60 to mesh with the rack 70. Similarly, the rack blade 50 may have a rack hinge 54 that seats the rack 70. The rack hinge 54 may be disposed at the outer circumference of the proximal portion of the rack blade 50. Because the rack 70 may be allowed to pivot about the rack blade 50, the rack 70 may stay within the rack guide 44 of the gear blade 40. For example, the rack 70 may stay meshed with the gear 60.

Each blade 30, 40, and 50 may be connected to a plurality (e.g., at least two) arms 80. Also for example, each arm 80 may be interconnected to other arms 80 in a circular cross pattern. For example, each arm 80 may be connected to three other arms 80 via arm pins 92. In at least some exemplary embodiments, each arm 80 may be connected to three other arms 80 via connection to an arm pin 92 at each end and another arm pin 92 at the center portion of each arm 80.

In at least some exemplary embodiments, one of the arms 80 (e.g., the first arm 80) may be connected to the first blade 30 via a relatively longer blade pin 90 being received in pin hole 31. For example, blade pin 90 may be longer than arm pin 92. One of the arms 80 may be connected to the gear blade 40 via the relatively longer blade pin 90 being received in pin hole 41. One of the arms 80 may be connected to the rack blade 50 via the relatively longer blade pin 90 being received in pin hole 51. This exemplary disclosed connection of arms 80 to blades 30, 40, and 50 may allow for the arms 80 that are connected to blades 30, 40, and 50 via blade pins 90 to rotate about the blades 30, 40, and 50. This exemplary disclosed connection of arms 80 to blades 30, 40, and 50 may also prevent the arms 80 that are connected to blades 30, 40, and 50 via blade pins 90 from translating relative to blades 30, 40, and 50. Another of the arms 80 (e.g., a second arm 80) may be connected to the first blade 30 via an elongated slot pin 91, which may be disposed and may be movable in (e.g., may ride inside) the pin slot 32. This may allow the arm 80 to rotate and translate based on slot pin 91 rotating and moving along the pin slot 32. Another of the arms 80 may be connected to the gear blade 40 via an elongated slot pin 91, which may be disposed and may be movable in (e.g., may ride inside) the pin slot 42. This may allow the arm 80 to rotate and translate based on slot pin 91 rotating and moving along the pin slot 42. Another of the arms 80 may be connected to the rack blade 50 via an elongated slot pin 91, which may be disposed and may be movable in (e.g., may ride inside) the pin slot 52. This may allow the arm 80 to rotate and translate based on slot pin 91 rotating and moving along the pin slot 52.

Figure 4:
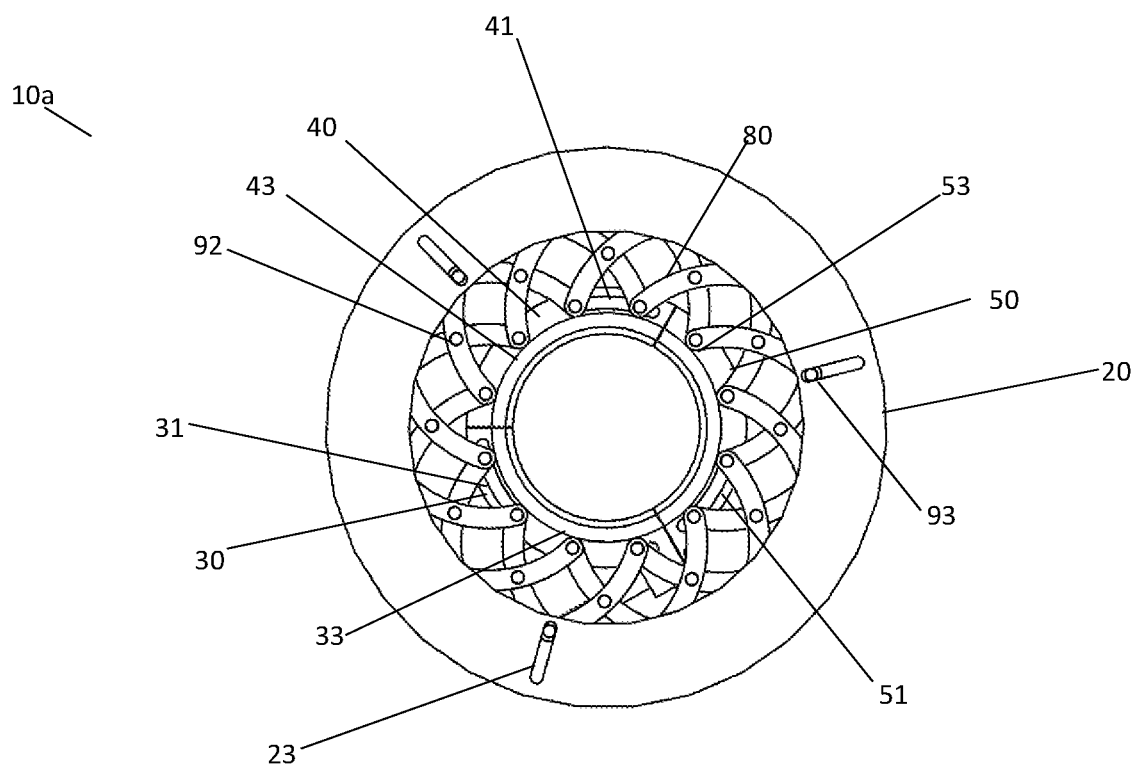
FIG. 4 illustrates a distal view of an exemplary disclosed retractor in a closed position.

In at least some exemplary embodiments (e.g., retractor 10a) and as illustrated in FIGS. 4 and 8, a plurality (e.g., a series) of pin slots 23 (e.g., annular member pin slots) may be disposed at the outer ring 20. Elongated ring pins 93 may extend through (e.g., through apertures of) a plurality (e.g., a pair) of arms 80 and into the pin slots 23. The elongated ring pins 93 may contribute to maintaining a desired (e.g., correct) orientation of the outer ring 20 relative to the blades 30, 40, and 50. It is also contemplated that a handle or mount (not shown for clarity) may be added to the outer ring 20 to keep the retractor 10 in a desired (e.g., specific) location.

The exemplary disclosed retractor may include any suitable number of blades such as, for example, three blades, four, blades, six blades, or any other desired number of blades. Also for example, a plurality of arms 80 may be movable (e.g., ride within) in pin slots 32, 42, and 52. Further for example, a plurality of ring pins 93 may extend into outer ring 20. Additionally for example, distal portion 33 of first blade 30, distal portion 43 of gear blade 40, and distal portion 53 of rack blade 50 may be detachable and/or extendable in order to adjust a depth of blades 30, 40, and 50 for example when disposed n a body portion of a patient.

The exemplary disclosed system, apparatus, and method may be used in any suitable application involving a surgical procedure (e.g., on a human or animal). For example, the exemplary disclosed system, apparatus, and method may be used in any suitable application involving holding an injured portion of a patient's body or incision open while a surgeon works on the patient. In at least some exemplary embodiments, the exemplary disclosed system, apparatus, and method may be used in any suitable application involving a lumbar retractor.

Figure 2:
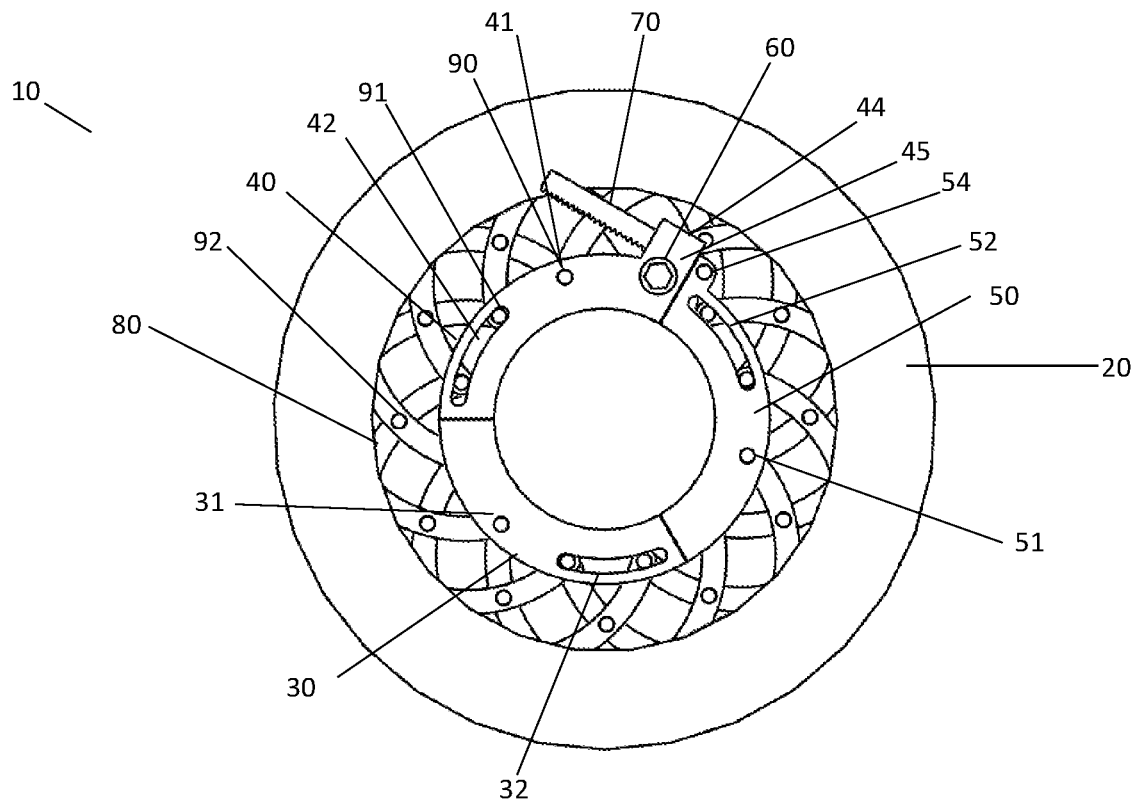
FIG. 2 illustrates a proximal view of an exemplary disclosed retractor in a closed position.
Figure 3:
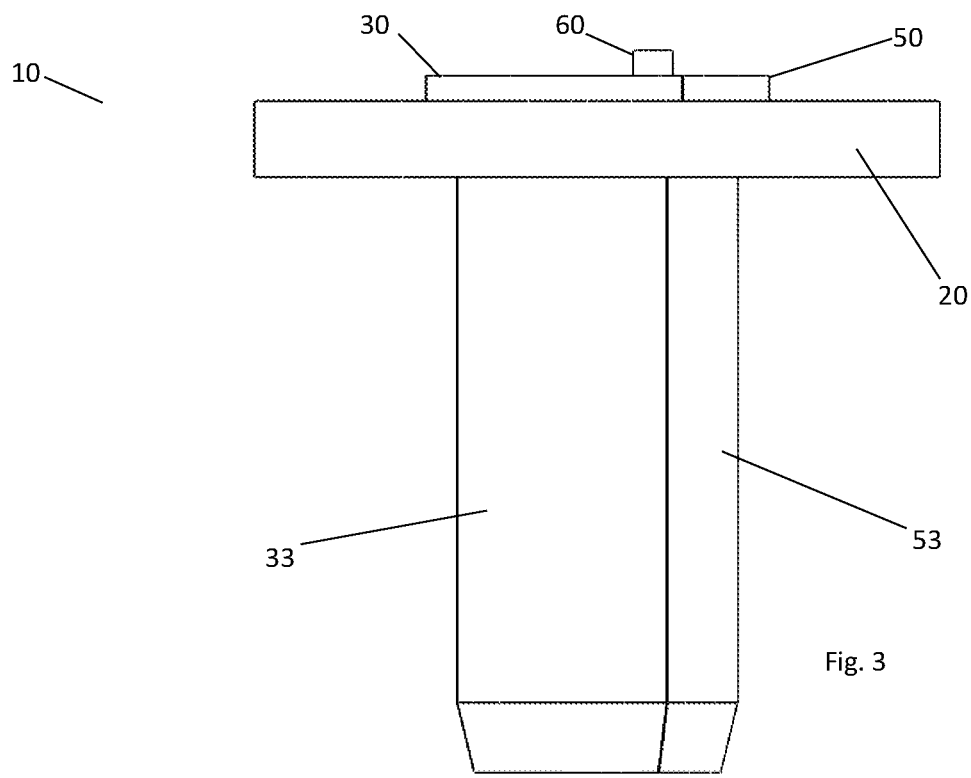
FIG. 3 illustrates a lateral view of an exemplary disclosed retractor in a closed position.
Figure 5:
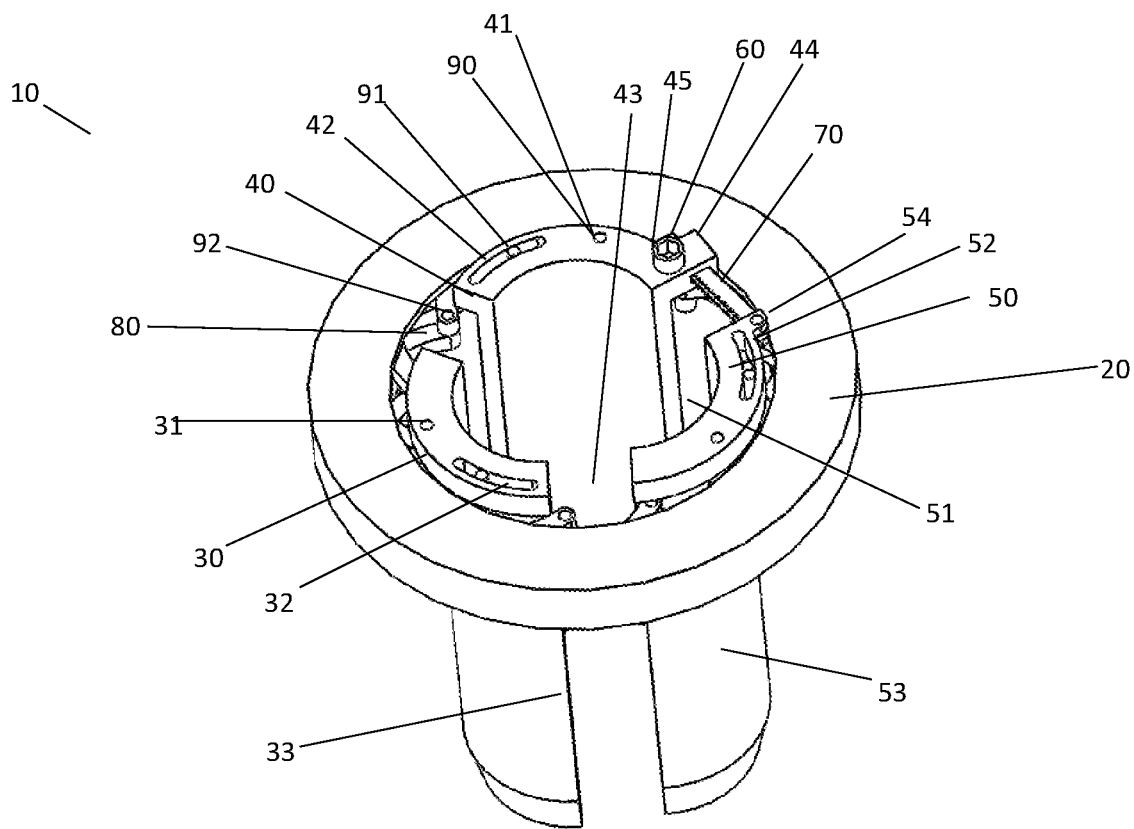
FIG. 5 illustrates a perspective view of a proximal face of an exemplary disclosed retractor in an open position.
Figure 6:
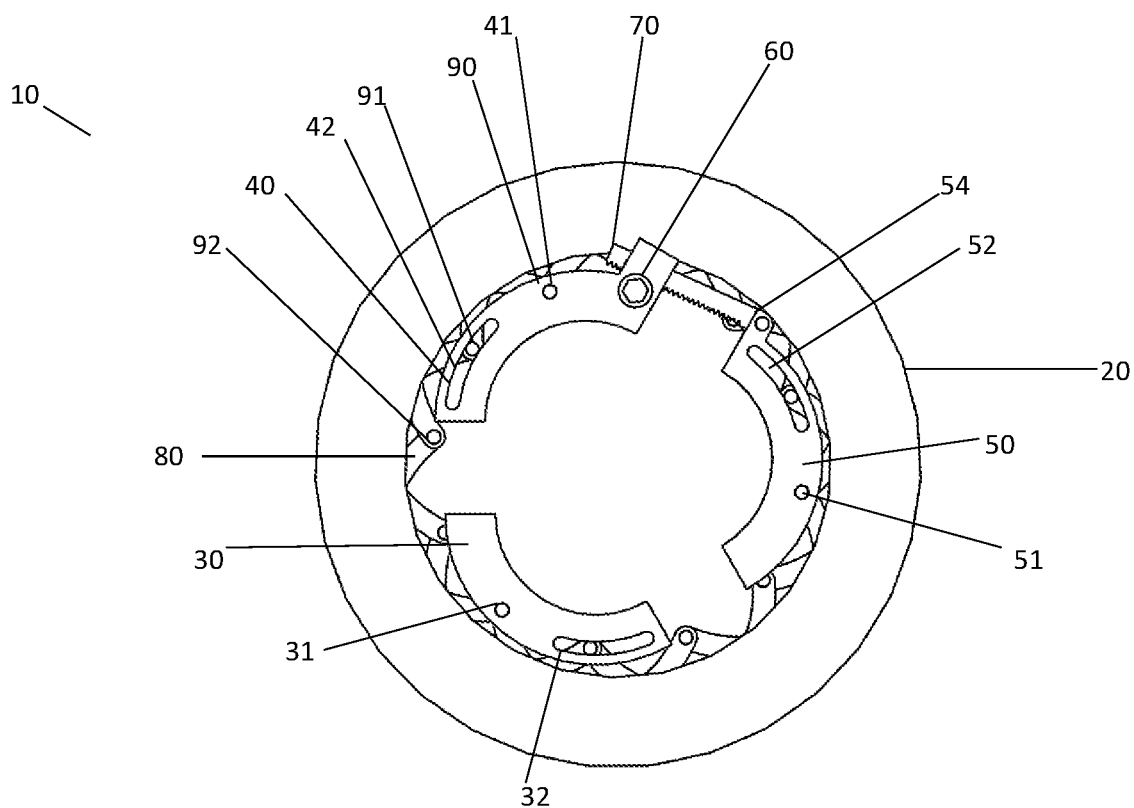
FIG. 6 illustrates a proximal view of an exemplary disclosed retractor in an open position.
Figure 9:
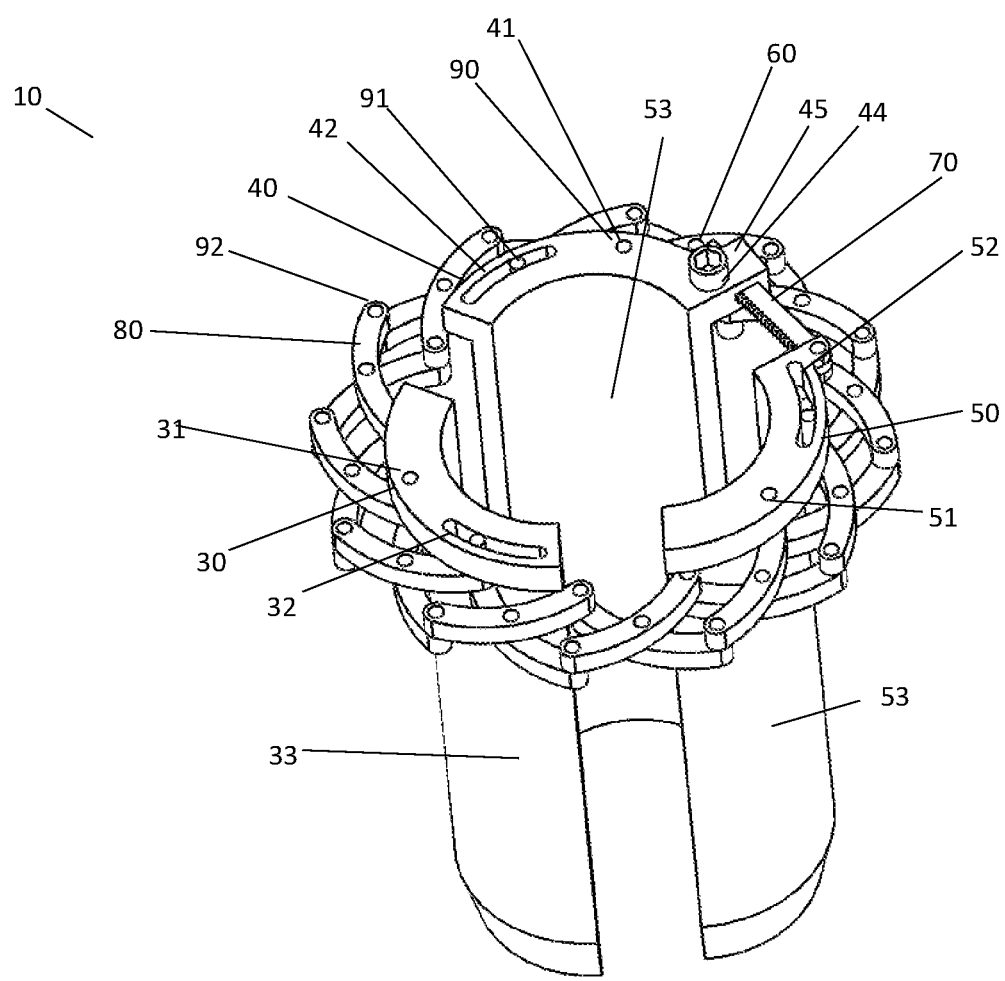
FIG. 9 illustrates a perspective view of a proximal face of an exemplary disclosed retractor with outer ring in an open position.

An exemplary operation of the exemplary disclosed system, apparatus, and method will now be described. The retractor 10 may be disposed in a closed position at a location of a patient's (e.g., or animal's) body (e.g., wound or incision) for example as illustrated in FIGS. 1-3. Once the retractor 10 is placed as desired, the gear 60 may be rotated. As the gear 60 is rotated, gear 60 operates to move (e.g., draw) the rack 70 through the rack guide 44, thereby pushing the gear blade 40 away from the rack blade 50. For example, the gear 60 may interact with (e.g., be meshed with) the rack 70 so that a rotation of the gear 60 may cause the rack 70 to move relative to the gear 60. Based on the gear blade 40 pushing away from the rack blade 50, the arms 80 may be compressed (e.g., compressed circumferentially) toward the position illustrated in FIGS. 5-7 and 9. For example, the arms 80 may be compressed in a circumferential direction or width as illustrated in the movement of the arms 80 from the first position of FIGS. 1 and 2 (e.g., relatively larger circumferential width of uncompressed arms 80) to the second position of FIGS. 5 and 6 (e.g., relatively smaller circumferential width of compressed arms 80). In at least some exemplary embodiments, the circumferential width may be the distance or width of the meshed band of arms 80 disposed between the blades 30, 40, and 50 and the outer ring 20 and may change between the uncompressed circumferential width (e.g., as illustrated in FIGS. 1 and 2) and the compressed circumferential width (e.g., as illustrated in FIGS. 5 and 6). For example, the arm members (e.g., arms 80) may have an uncompressed circumferential width when the blades 30, 40, and 50 are in the first position as illustrated for example in FIGS. 1 and 2, and the arms 80 may have a compressed circumferential width that is smaller than the uncompressed circumferential width when the blades 30, 40, and 50 are in the second position illustrated for example in FIGS. 5 and 6. Also for example, moving the arms 80 between the uncompressed circumferential width and the compressed circumferential width may include rotating a first center portion of a first arm 80 about an arm pin 92 that rotatably attaches the first center portion to a second center portion of a second arm 80.

As the arms 80 are compressed (e.g., compressed circumferentially), the first blade 30 may also be pushed away from the blades 40 and 50 toward the open position illustrated in FIGS. 5-7 and 9. As the arms 80 are compressed, the blades 30, 40, and 50 may be drawn outwardly at substantially the same time. The blades 30, 40, and 50 may thereby apply an even pressure against soft tissue surrounding the retractor 10 when disposed in a patient's or animal's body. For example, based on the configuration of the attachment of the arms 80 to the blades 30, 40, and 50, as any one of the blades 30, 40, and 50 moves, then all of the blades 30, 40, and 50 move (e.g., move equidistantly). For example, moving the blades 30, 40, and 50 from the first position (e.g., closed position for example as illustrated in FIGS. 1-3) to the second position (e.g., open position for example as illustrated in FIGS. 5-7) may include maintaining equidistance between the blades 30, 40, and 50 as the blades 30, 40, and 50 move from the first position to the second position. For example, a distance between blades 30, 40, and 50 may increase equidistantly from each other as blades 30, 40, and 50 move from the first position (e.g., closed position for example as illustrated in FIGS. 1-3) to the second position (e.g., open position for example as illustrated in FIGS. 5-7). The distal portions 33, 43, and 53 may thereby move equidistantly and retract the soft tissue surrounding the retractor 10 evenly (e.g., applying substantially equal pressure to the surrounding soft tissue). The retractor 10a may operate similar to the retractor 10, moving from the closed position illustrated in FIG. 4 to the open position illustrated in FIG. 8.

A list of exemplary parts of the exemplary disclosed system, apparatus, and method is provided below:
10—retractor
10a—retractor
20—outer ring
   21—outer shell
   22—hollow interior
   23—pin slot
30—blade
   31—pin hole
   32—pin slot
   33—distal portion
40—gear blade
   41—pin hole
   42—pin slot
   43—distal portion
   44—rack guide
   45—gear hole
50—rack blade
   51—pin hole
   52—pin slot
   53—distal portion
   54—rack hinge
60—gear
70—rack
80—arm
90—blade pin
91—slot pin
92—arm pin
93—ring pin In at least some exemplary embodiments, the exemplary disclosed method may include providing a plurality of blades (e.g., blades 30, 40, and 50), movably connecting the plurality of blades to an outer member (e.g., outer ring 20) via a plurality of arm members (e.g., arms 80), disposing the plurality of blades in a human or animal body, and moving the plurality of blades from a first position outward to a second position when the plurality of blades are disposed in the human or animal body. The plurality of blades may be disposed further from each other in the second position than the first position. Moving the plurality of blades outward from the first position to the second position may include moving the plurality of arm members. Moving the plurality of blades includes maintaining equidistance between the plurality of blades as the plurality of blades move from the first position to the second position. Moving the plurality of blades from the first position outward to the second position may include rotating a gear disposed on a gear blade of the plurality of blades that draws a rack rotatably attached to a rack blade of the plurality of blades through a rack guide disposed in the gear blade. The plurality of arm members may have an uncompressed circumferential width when the plurality of blades are in the first position, and the plurality of arm members may have a compressed circumferential width that is smaller than the uncompressed circumferential width when the plurality of blades are in the second position. Moving the plurality of arm members between the uncompressed circumferential width and the compressed circumferential width may include rotating a first center portion of a first arm member of the plurality of arm members about an arm pin that rotatably attaches the first center portion to a second center portion of a second arm member of the plurality of arm members. Maintaining equidistance between the plurality of blades as the plurality of blades move from the first position to the second position may include rotating at least some of first end portions of the plurality of arm members relative to the plurality of blades about a plurality of blade pins, rotating at least some of center portions of the plurality of arm members relative to each other about a first plurality of arm pins, and rotating at least some of second end portions of the plurality of arm members relative to the outer member about a second plurality of arm pins. Maintaining equidistance between the plurality of blades as the plurality of blades move from the first position to the second position may further include attaching at least some of the first end portions of the plurality of arm members to the plurality of blades via a plurality of slot pins that are configured to rotate and translate in a plurality of pin slots of the plurality of blades. Maintaining equidistance between the plurality of blades as the plurality of blades move from the first position to the second position may further include attaching at least some of the second end portions of the plurality of arm members to the outer member via a plurality of ring pins that are configured to rotate and translate in a plurality of annular member pin slots of the outer member. Moving the plurality of blades from the first position outward to the second position may include moving the plurality of blades equidistantly relative to each other from the first position, in which the plurality of blades may contact each other to form a ring, to the second position in which the plurality of blades may be disposed away from each other. The exemplary disclosed method may also include moving the plurality of blades from the second position to the first position while maintaining equidistance relative to each other.

In at least some exemplary embodiments, the exemplary disclosed retractor may include an annular member (e.g., outer ring 20) including a hollow interior, a first blade (e.g., first blade 30), a gear blade (e.g., gear blade 40), and a rack blade (e.g., rack blade 50) disposed in the hollow interior, a first plurality of arm members (e.g., arms 80) rotatably connecting the first blade to the annular member, a second plurality of arm members (e.g., arms 80) rotatably connecting the gear blade to the annular member, and a third plurality of arm members (e.g., arms 80) rotatably connecting the rack blade to the annular member. At least one of the first plurality of arm members may be either attached to the first blade via a first slot pin that is configured to rotate and translate in a first pin slot of the first blade, or attached to the annular member via a first ring pin that is configured to rotate and translate in a first annular member pin slot of the annular member. At least one of the second plurality of arm members may be attached to the annular member via a second ring pin that is configured to rotate and translate in a second annular member pin slot of the annular member. At least one of the third plurality of arm members may be attached to the annular member via a third ring pin that is configured to rotate and translate in a third annular member pin slot of the annular member. At least one of the second plurality of arm members may be attached to the gear blade via a second slot pin that is configured to rotate and translate in a second pin slot of the gear blade. At least one of the third plurality of arm members may be attached to the rack blade via a third slot pin that is configured to rotate and translate in a third pin slot of the rack blade. The exemplary disclosed retractor may also include a gear and a rack guide disposed at the gear blade and a rack attached to the rack blade. The rack may be attached to the rack blade via a hinge. As the gear is rotated, the gear may be configured to draw the rack through the rack guide, which moves the gear blade away from the rack blade. A first center portion of at least one of the first plurality of arm members may be rotatably attached via a first arm pin to a second center portion of another of the first plurality of arm members. A third center portion of at least one of the second plurality of arm members may be rotatably attached via a second arm pin to a fourth center portion of another of the second plurality of arm members. A fifth center portion of at least one of the third plurality of arm members may be rotatably attached via a third arm pin to a sixth center portion of another of the third plurality of arm members.

In at least some exemplary embodiments, the exemplary disclosed method may include providing at least three blades (e.g., blades 30, 40, and 50), movably connecting the at least three blades to an outer member (e.g., outer ring 20) via a plurality of arm members (e.g., arms 80), disposing the at least three blades in a human or animal body, and moving the at least three blades from a first position outward to a second position when the at least three blades are disposed in the human or animal body. The at least three blades may be disposed further from each other in the second position than the first position. Moving the at least three blades outward from the first position to the second position may include moving the plurality of arm members. Moving the at least three blades may include maintaining equidistance between the at least three blades as the at least three blades move from the first position to the second position. Maintaining equidistance between the at least three blades as the at least three blades move from the first position to the second position may include rotating at least some of first end portions of the plurality of arm members relative to the at least three blades about a plurality of blade pins, rotating at least some of center portions of the plurality of arm members relative to each other about a first plurality of arm pins, and rotating at least some of second end portions of the plurality of arm members relative to the outer member about a second plurality of arm pins. Maintaining equidistance between the at least three blades as the at least three blades move from the first position to the second position may further include attaching at least some of the first end portions of the plurality of arm members to the at least three blades via a plurality of slot pins that are configured to rotate and translate in a plurality of pin slots of the at least three blades.

The exemplary disclosed system, apparatus, and method may provide an efficient and effective technique for holding an injured portion of a patient's body or incision open while a surgeon works on the patient. The exemplary disclosed system, apparatus, and method may provide for even pressure on soft tissue around the retractor, reducing or substantially preventing bruising and post-surgical pain. Also, the exemplary disclosed system, apparatus, and method may reduce an amount of time involved in expanding the blades of a retractor. Further, the exemplary disclosed system, apparatus, and method may provide a compact retractor that may not obstruct a surgeon while working on a patient or x-ray and other imaging that may be performed during a procedure.

While multiple embodiments are disclosed, still other embodiments of the present disclosure will become apparent to those skilled in the art from this detailed description. There may be aspects of this disclosure that may be practiced without the implementation of some features as they are described. It should be understood that some details have not been described in detail in order to not unnecessarily obscure the focus of the disclosure. The disclosure is capable of myriad modifications in various obvious aspects, all without departing from the spirit and scope of the present disclosure. Accordingly, the drawings and descriptions are to be regarded as illustrative rather than restrictive in nature.

What is claimed is:

1. A method, comprising:
   providing a plurality of blades;
   movably connecting the plurality of blades to an outer member via a plurality of arm members;
   disposing the plurality of blades in a human or animal body; and
   moving the plurality of blades from a first position outward to a second position when the plurality of blades are disposed in the human or animal body;
   wherein the plurality of blades are disposed further from each other in the second position than the first position;
   wherein moving the plurality of blades from the first position outward to the second position includes rotating a gear disposed on a gear blade of the plurality of blades that draws a rack rotatably attached to a rack blade of the plurality of blades through a rack guide disposed in the gear blade;
   wherein moving the plurality of blades outward from the first position to the second position includes moving the plurality of arm members; and
   wherein moving the plurality of blades includes maintaining equidistance between the plurality of blades as the plurality of blades move from the first position to the second position.

2. The method of claim 1, wherein the plurality of arm members have an uncompressed circumferential width when the plurality of blades are in the first position, and the plurality of arm members have a compressed circumferential width that is smaller than the uncompressed circumferential width when the plurality of blades are in the second position.

3. The method of claim 2, wherein moving the plurality of arm members between the uncompressed circumferential width and the compressed circumferential width includes rotating a first center portion of a first arm member of the plurality of arm members about an arm pin that rotatably attaches the first center portion to a second center portion of a second arm member of the plurality of arm members.

4. The method of claim 1, wherein maintaining equidistance between the plurality of blades as the plurality of blades move from the first position to the second position includes rotating at least some of first end portions of the plurality of arm members relative to the plurality of blades about a plurality of blade pins, rotating at least some of center portions of the plurality of arm members relative to each other about a first plurality of arm pins, and rotating at least some of second end portions of the plurality of arm members relative to the outer member about a second plurality of arm pins.

5. The method of claim 4, wherein maintaining equidistance between the plurality of blades as the plurality of blades move from the first position to the second position further includes attaching at least some of the first end portions of the plurality of arm members to the plurality of blades via a plurality of slot pins that are configured to rotate and translate in a plurality of pin slots of the plurality of blades.

6. The method of claim 4, wherein maintaining equidistance between the plurality of blades as the plurality of blades move from the first position to the second position further includes attaching at least some of the second end portions of the plurality of arm members to the outer member via a plurality of ring pins that are configured to rotate and translate in a plurality of annular member pin slots of the outer member.

7. The method of claim 1, wherein moving the plurality of blades from the first position outward to the second position includes moving the plurality of blades equidistantly relative to each other from the first position, in which the plurality of blades contact each other to form a ring, to the second position in which the plurality of blades are disposed away from each other.

8. The method of claim 1, further comprising moving the plurality of blades from the second position to the first position while maintaining equidistance relative to each other.

9. A retractor, comprising:
an annular member including a hollow interior;
a first blade, a gear blade, and a rack blade disposed in the hollow interior;
a first plurality of arm members rotatably connecting the first blade to the annular member;
a second plurality of arm members rotatably connecting the gear blade to the annular member; and
a third plurality of arm members rotatably connecting the rack blade to the annular member;
wherein at least one of the first plurality of arm members is either attached to the first blade via a first slot pin that is configured to rotate and translate in a first pin slot of the first blade, or attached to the annular member via a first ring pin that is configured to rotate and translate in a first annular member pin slot of the annular member.

10. The retractor of claim 9, wherein:
at least one of the second plurality of arm members is attached to the annular member via a second ring pin that is configured to rotate and translate in a second annular member pin slot of the annular member; and
at least one of the third plurality of arm members is attached to the annular member via a third ring pin that is configured to rotate and translate in a third annular member pin slot of the annular member.

11. The retractor of claim 9, wherein:
at least one of the second plurality of arm members is attached to the gear blade via a second slot pin that is configured to rotate and translate in a second pin slot of the gear blade; and
at least one of the third plurality of arm members is attached to the rack blade via a third slot pin that is configured to rotate and translate in a third pin slot of the rack blade.

12. The retractor of claim 9, further comprising a gear and a rack guide disposed at the gear blade and a rack attached to the rack blade.

13. The retractor of claim 12, wherein the rack is attached to the rack blade via a hinge.

14. The retractor of claim 12, wherein as the gear is rotated, the gear is configured to draw the rack through the rack guide, which moves the gear blade away from the rack blade.

15. The retractor of claim 9, wherein a first center portion of at least one of the first plurality of arm members is rotatably attached via a first arm pin to a second center portion of another of the first plurality of arm members.

16. The retractor of claim 15, wherein:
a third center portion of at least one of the second plurality of arm members is rotatably attached via a second arm pin to a fourth center portion of another of the second plurality of arm members; and
a fifth center portion of at least one of the third plurality of arm members is rotatably attached via a third arm pin to a sixth center portion of another of the third plurality of arm members.

17. A method, comprising:
providing at least three blades;
movably connecting the at least three blades to an outer member via a plurality of arm members;
disposing the at least three blades in a human or animal body; and
moving the at least three blades from a first position outward to a second position when the at least three blades are disposed in the human or animal body;
wherein the at least three blades are disposed further from each other in the second position than the first position;
wherein moving the at least three blades outward from the first position to the second position includes moving the plurality of arm members;
wherein moving the at least three blades includes maintaining equidistance between the at least three blades as the at least three blades move from the first position to the second position; and
wherein maintaining equidistance between the at least three blades as the at least three blades move from the first position to the second position includes rotating at least some of first end portions of the plurality of arm members relative to the at least three blades about a plurality of blade pins, rotating at least some of center portions of the plurality of arm members relative to each other about a first plurality of arm pins, and rotating at least some of second end portions of the plurality of arm members relative to the outer member about a second plurality of arm pins.

18. The method of claim 17, wherein maintaining equidistance between the at least three blades as the at least three blades move from the first position to the second position further includes attaching at least some of the first end portions of the plurality of arm members to the at least three blades via a plurality of slot pins that are configured to rotate and translate in a plurality of pin slots of the at least three blades.

\* \* \* \* \*